(12) United States Patent
Hiraga et al.

(10) Patent No.: US 10,016,157 B2
(45) Date of Patent: Jul. 10, 2018

(54) NON-TRANSITORY COMPUTER-READABLE, DETECTION METHOD, AND DETECTION DEVICE

(71) Applicants: FUJITSU LIMITED, Kawasaki-shi, Kanagawa (JP); TRANSTRON INC., Yokohama-shi, Kanagawa (JP)

(72) Inventors: Norio Hiraga, Ota (JP); Masatsugu Isogai, Yokohama (JP); Tomoyuki Tsuda, Yokohama (JP)

(73) Assignees: FUJITSU LIMITED, Kawasaki (JP); TRANSTRON INC., Yokohama-shi (JP)

( * ) Notice: Subject to any disclaimer, the term of this patent is extended or adjusted under 35 U.S.C. 154(b) by 71 days.

(21) Appl. No.: 15/164,314

(22) Filed: May 25, 2016

(65) Prior Publication Data
US 2016/0361007 A1 Dec. 15, 2016

(30) Foreign Application Priority Data

Jun. 9, 2015 (JP) .................................. 2015-116807

(51) Int. Cl.
| G08B 23/00 | (2006.01) |
| A61B 5/18 | (2006.01) |
| A61B 5/00 | (2006.01) |
| A61B 5/01 | (2006.01) |
| A61B 5/021 | (2006.01) |
| A61B 5/08 | (2006.01) |

(52) U.S. Cl.
CPC .............. *A61B 5/18* (2013.01); *A61B 5/0022* (2013.01); *A61B 5/01* (2013.01); *A61B 5/021* (2013.01); *A61B 5/082* (2013.01); *A61B 5/4815* (2013.01); *A61B 5/6893* (2013.01); *A61B 5/7275* (2013.01); *A61B 5/7282* (2013.01)

(58) Field of Classification Search
CPC ........... A61B 5/10; G08B 21/06; B60K 28/06
USPC ................................................... 340/575, 576
See application file for complete search history.

(56) References Cited

U.S. PATENT DOCUMENTS

| 6,575,902 | B1 * | 6/2003 | Burton | ..................... A61B 5/18 340/575 |
| 7,359,821 | B1 * | 4/2008 | Smith | .................... G07C 5/002 702/113 |
| 9,019,093 | B2 * | 4/2015 | Wendt | ................... B60W 50/14 340/439 |
| 2005/0030184 | A1 * | 2/2005 | Victor | .................... B60K 28/06 340/576 |
| 2006/0253307 | A1 * | 11/2006 | Warren | .................. G06Q 40/08 705/4 |

(Continued)

FOREIGN PATENT DOCUMENTS

JP 2014-199616 A 10/2014

*Primary Examiner* — Eric M Blount
(74) *Attorney, Agent, or Firm* — Westerman, Hattori, Daniels & Adrian, LLP

(57) ABSTRACT

A detection device acquires traveling information and identification information of a driver from a first device installed in a vehicle and acquires a vital sign and the identification information of the driver from a second device that monitors the vital sign. The detection device determines probability of detecting a predetermined event, based on the vital sign in proximity of a certain time, when the predetermined event is detected at the certain time based on the traveling information and outputs a determination result.

6 Claims, 7 Drawing Sheets

(56) References Cited

U.S. PATENT DOCUMENTS

| | | | |
|---|---|---|---|
| 2007/0008151 A1* | 1/2007 | Victor | A61B 5/11 340/573.1 |
| 2010/0241021 A1* | 9/2010 | Morikawa | A61B 5/048 600/544 |
| 2012/0123806 A1* | 5/2012 | Schumann, Jr. | G06Q 40/08 705/4 |
| 2013/0073115 A1* | 3/2013 | Levin | A61B 5/18 701/1 |
| 2014/0292539 A1 | 10/2014 | Omiya et al. | |

* cited by examiner

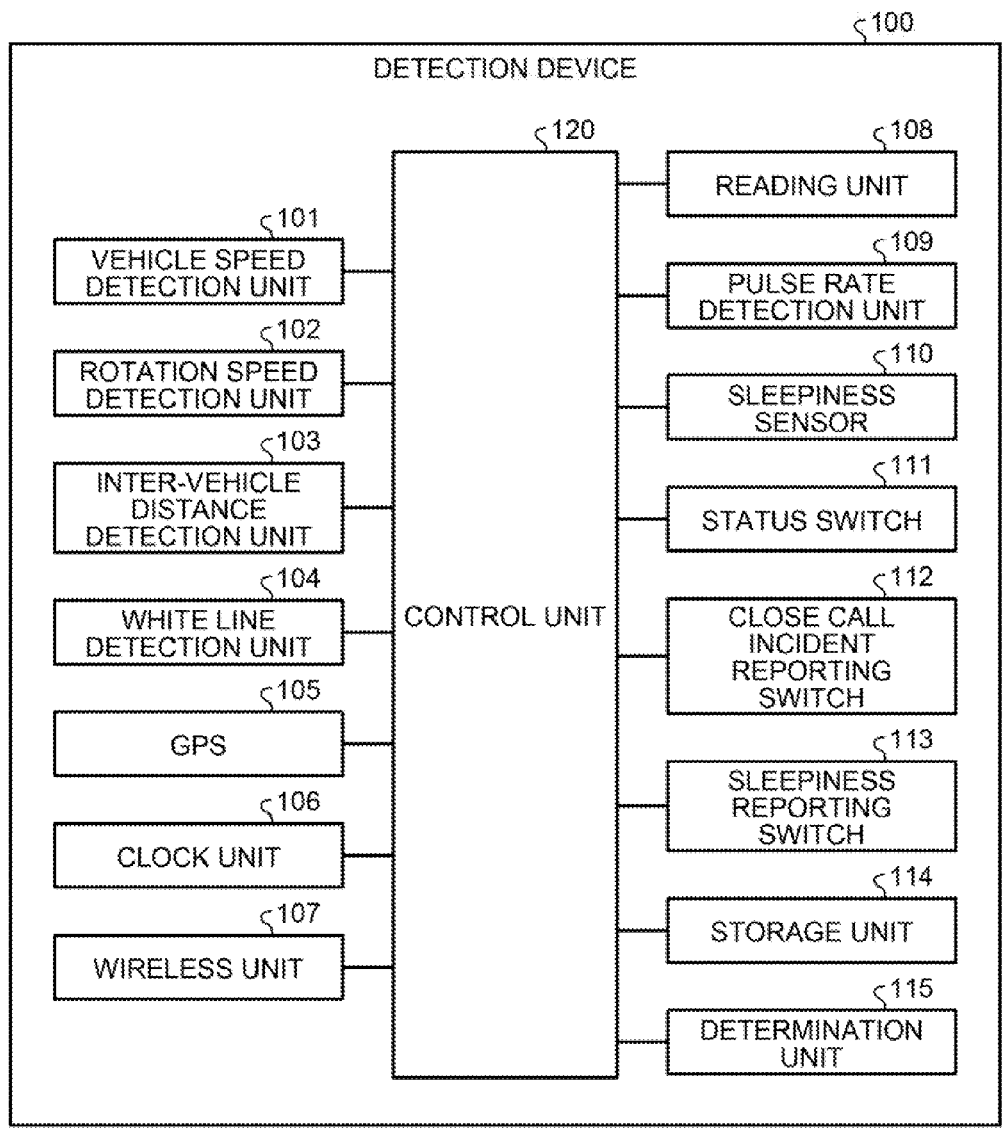

FIG.4

| USER ID | DATE AND TIME OF MEASURE-MENT | BLOOD PRESSURE | PULSE RATE | DETECTED SLEEPINESS | OPERA-TION FLAG | WHITE LINE DEVIATION | CLOSE CALL | OFFENSE | TAIL-GATING | TRAVELING SPEED | TRAVELING DISTANCE | ENGINE ROTATION SPEED |
|---|---|---|---|---|---|---|---|---|---|---|---|---|
| XXXXX1 | 2014/11/12 9:00:00 | 122/72 | | | | | | | | 0 km/h | 0 km | 0 rpm |
| XXXXX1 | 2014/11/12 9:01:00 | | | | 1 | | | | | X1 km/h | X11 km | X21 rpm |
| XXXXX1 | 2014/11/12 9:02:00 | | | | | | | | | X2 km/h | X12 km | X22 rpm |
| ... | ... | ... | ... | ... | ... | ... | ... | ... | ... | ... | ... | ... |
| XXXXX1 | 2014/11/12 13:15:05 | | | | | | | | | X3 km/h | X13 km | X23 rpm |
| XXXXX1 | 2014/11/12 13:20:05 | | | | | | | | 1 | X4 km/h | X14 km | X24 rpm |
| XXXXX1 | 2014/11/12 14:30:05 | | | | | | | | 1 | X5 km/h | X15 km | X25 rpm |
| ... | ... | ... | ... | ... | ... | ... | ... | ... | ... | ... | ... | ... |
| XXXXX1 | 2014/11/12 14:30:05 | | | | | | 1 | 1 | | X6 km/h | X16 km | X26 rpm |
| ... | ... | ... | ... | ... | ... | ... | ... | ... | ... | ... | ... | ... |
| XXXXX1 | 2014/11/12 19:20:05 | | | | | | | | | X7 km/h | X17 km | X27 rpm |
| XXXXX1 | 2014/11/12 19:25:05 | | | | 0 | | | | | X8 km/h | X18 km | X28 rpm |
| XXXXX1 | 2014/11/12 19:48:05 | | | | | | | | | 0 km/h | 0 km | 0 rpm |
| XXXXX1 | 2014/11/12 19:59:05 | 120/70 | | | | | | | | 0 km/h | 0 km | 0 rpm |
| ... | ... | ... | ... | ... | ... | ... | ... | ... | ... | ... | ... | ... |

FIG.5

| USER ID | EVENT DETECTED DATE AND TIME | EVENT | PROBABILITY |
|---|---|---|---|
| XXXX1 | 2014/11/12/12:30 | OFFENSE | PROBABILITY A |
| XXXX1 | 2014/11/12/14:30 | OFFENSE | PROBABILITY C |
| XXXX1 | 2014/11/12/15:40 | OFFENSE | PROBABILITY A |
| ⋮ | | | |
| XXXX1 | 2014/11/12/20:30 | WHITE LINE DEVIATION | PROBABILITY A |
| XXXX1 | 2014/11/12/19:30 | OFFENSE | PROBABILITY B |
| ⋮ | | | |

114b

NON-TRANSITORY COMPUTER-READABLE, DETECTION METHOD, AND DETECTION DEVICE

CROSS-REFERENCE TO RELATED APPLICATIONS

This application is based upon and claims the benefit of priority of the prior Japanese Patent Application No. 2015-116807, filed on Jun. 9, 2015, the entire contents of which are incorporated herein by reference.

FIELD

The embodiment discussed herein is related to a computer-readable recording medium and the like.

BACKGROUND

In recent years, the number of fatalities caused by traffic accidents has been on the decline. However, the number of fatalities caused by company vehicles such as a truck is increasing slightly. Thus, for example, there is a conventional technology that analyses where and when accidents are likely to occur, based on traveling information, by recommending equipping company vehicles with a traveling recorder. For example, in such a conventional technology, a predetermined event such as abrupt braking and a white line deviation is detected based on the traveling information. Then, by using information such as where and when the detected predetermined event has occurred, measures are takers to reduce traffic accidents. A conventional example is described in Japanese Laid-open Patent Publication No. 2014-199616.

However, the conventional technology described above has a problem in that it is not possible to determine the probability of the detected predetermined event.

SUMMARY

According to an aspect of an embodiment, a non-transitory computer-readable recording medium stores therein a program that causes a computer to execute a process including acquiring traveling information and identification information of a driver from a first device installed in a vehicle; acquiring a vital sign and the identification information of the driver from a second device that monitors the vital sign; determining probability of detecting a predetermined event, based on the vital sign in proximity of a certain time, when the predetermined event is detected at the certain time based on the traveling information; and outputting a determination result.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 3 is a functional block diagram illustrating a configuration of a detection device;

FIG. 4 is an exemplary diagram illustrating a data configuration of driving information;

FIG. 5 is an exemplary diagram illustrating a data configuration of event probability information;

DESCRIPTION OF EMBODIMENT

Preferred embodiments of the present invention will be explained with reference to accompanying drawings. It is to be noted that the invention is net limited to the embodiment.

Figure 1:
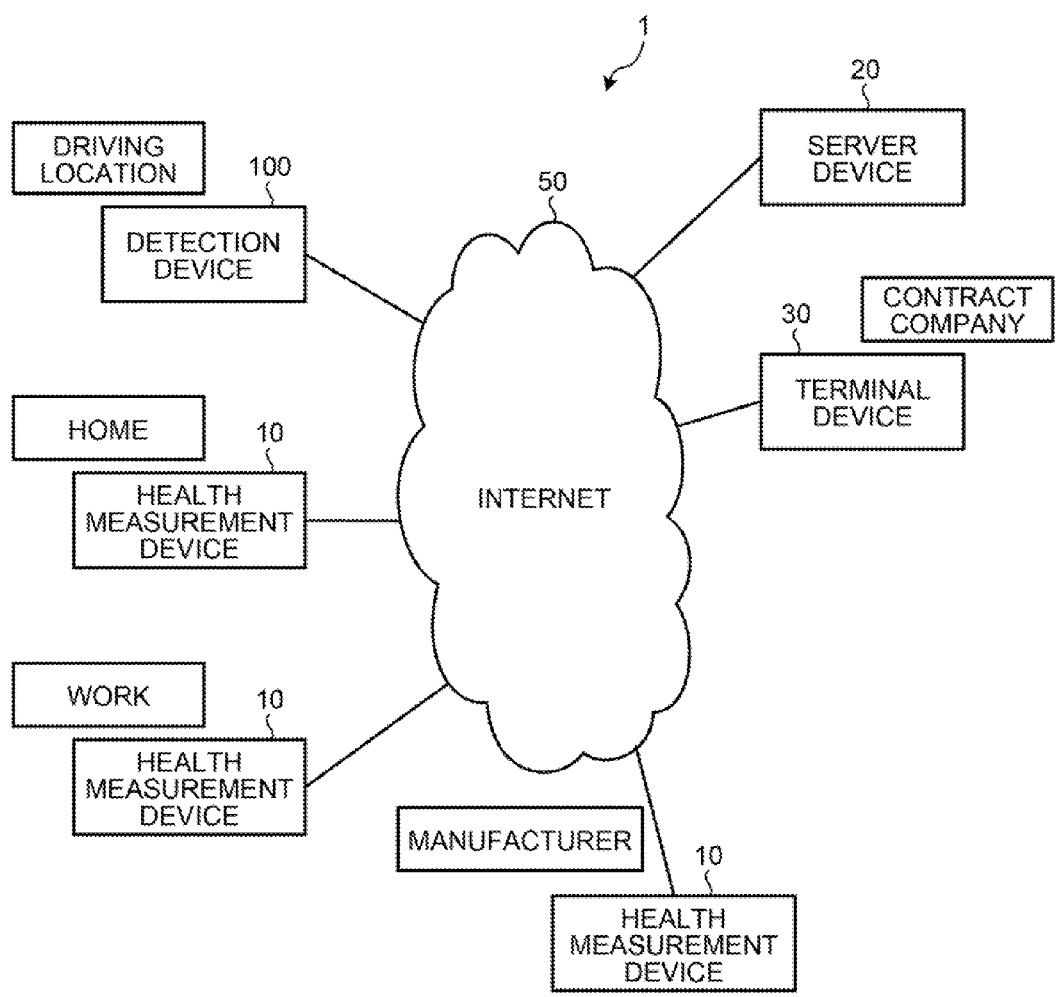
FIG. 1 is an exemplary diagram illustrating a system according to a present embodiment.

An example of a configuration of a system according to a present embodiment will now be described. FIG. 1 is an exemplary diagram illustrating a system according to a present embodiment. As illustrated in FIG. 1, a system 1 includes a plurality of health measurement devices 10, a server device 20, a plurality of terminal devices 30, and a plurality of detection devices 100. The health measurement devices 10, the server device 20, the terminal devices 30, and the detection devices 100 are mutually connected via an Internet 50.

For example, each of the health measurement devices 10 is a device that measures biological information of a driver who is at home, at work, and at ether places. For example, the health measurement device 10 is a measurement device such as a blood pressure meter, a weight scale, a clinical thermometer, an alcohol sensor, and a sleep measurement device.

The server device 20 communicably connects with each of the detection devices 100, which will be described below, via the Internet 50, and obtains driving information of drivers. The server device 20 communicably connects with the health measurement device 10 via the Internet, and obtains biological information of drivers. The server device 20 holds the driving information and the biological information of the drivers obtained from the detection device 100 and the health measurement device 10. The server device 20 then responds to a request from each of the terminal devices 30, and notifies the terminal device 30 of the driving information and the biological information of each of the drivers.

For example, the terminal device 30 is a terminal device such as a personal computer placed in a transportation company and the like. For example, the terminal device 30 requests the server device 20 to transmit the driving information and the biological information of a driver, and receives the requested driving information and biological information of the driver from the server device 20.

The detection device 100 is a device mounted on a driver's seat of a vehicle, and detects the driving information of the driver of the vehicle. The detection device 100 notifies the server device 20 of the detected driving information. If a predetermined event is detected from the driving information related to the driving of the vehicle, the detection device 100 determines the probability of the predetermined event, depending on whether a vital sign value of the driver in the proximity of the time when the predetermined event has occurred is different from a normal value.

An example of a configuration of the health measurement device 10 illustrated in FIG. 1 will now be described. FIG.

Figure 2:
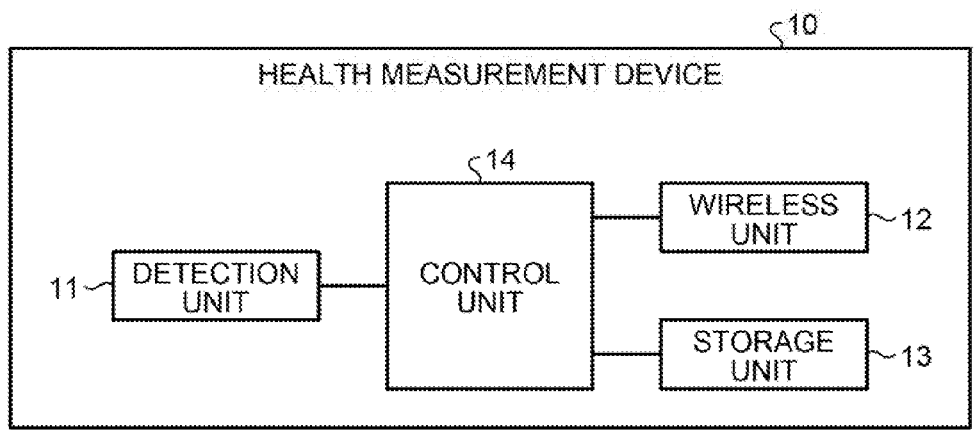
FIG. 2 is a functional block diagram illustrating a configuration of a health measurement device.

2 is a functional block diagram illustrating a configuration of a health measurement device. As illustrated in FIG. 2, the health measurement device 10 includes a detection unit 11, a wireless unit 12, a storage unit 13, and a control unit 14.

The detection unit 11 detects biological information of a user. For example, if the health measurement device 10 is a pulse monitor, the detection unit 11 measures the pulse rate of the user. For example, the detection unit 11 is a contact type pulse measurement unit such as an ear clip type pulse measurement unit that comes into contact with the body of the user, or a non-contact type pulse measurement unit. If the health measurement device 10 is a blood pressure meter, the detection unit 11 measures the blood pressure of the user. For example, the detection unit 11 is a contact type blood pressure measurement unit or a non-contact type blood pressure measurement unit. For example, if the health measurement device 10 is a weight scale, the detection unit 11 measures the weight of the user. For example, the detection unit 11 is a contact type weight measurement unit or a non-contact type weight measurement unit. For example, if the health measurement device 10 is a clinical thermometer, the detection unit 11 measures the body temperature of the user. For example, the detection unit 11 is a contact type body temperature measurement unit or a non-contact type body temperature measurement unit. For example, if the health measurement device 10 is a measurement device that detects an alcohol concentration in the breath, the detection unit 11 is a measurement unit that measures the alcohol concentration in the breath of the user. If the health measurement device 10 is a sleep measurement device, the defection unit 11 is a measurement unit that measures the sleeping quality of the user.

For example, the wireless unit 12 is a communication interface communicably connected to the Internet 50 in a wireless manner. If the wireless unit 12 is not built in the health measurement device 10, the health measurement device 10 may fee provided with a function capable of communicably connecting to the Internet 50, by using a terminal device such as a smartphone. The storage unit 13 is an area to store therein biological information for each user ID to identify the user of the health measurement device 10 and for each date and time of measurement. The control unit 14 is a processing unit that controls the entire health measurement device 10. The control unit 14 stores the biological information for each user ID to identify the user of the health measurement device 10 and for each date and time of measurement, in the storage unit 13.

An example of a configuration of the detection device 100 illustrated in FIG. 1 will now be described. FIG. 3 is a functional block diagram illustrating a configuration of a detection device. As illustrated in FIG. 3, the detection device 100 includes a vehicle speed detection unit 101, a rotation speed detection unit 102, an inter-vehicle distance detection unit 103, a white line detection unit 104, a global positioning system (GPS) 105, and a clock unit 106. The detection device 100 also includes a wireless unit 107, a reading unit 108, a pulse rate detection unit 109, a sleepiness sensor 110, a status switch 111, and a close call incident reporting switch 112. The detection device 100 further includes a sleepiness reporting switch 113, a storage unit 114, a determination unit 115, and a control unit 120.

For example, the vehicle speed detection unit 101 is a detection unit that detects the traveling speed and the traveling distance of a vehicle, through the sensor and the like installed in the vehicle. For example, the rotation speed detection unit 102 is a detection unit that detects the engine rotation speed of the vehicle, through the sensor installed in the vehicle. For example, the inter-vehicle distance detection unit 103 is a detection unit that detects the inter-vehicle distance to the preceding vehicle, through the sensor installed in the vehicle. For example, the white line detection unit 104 is a detection unit that detects the deviation of the vehicle from the white line that is a lane on a road, through the sensor installed in the vehicle. The GPS 105 is a system that measures the current position of the vehicle.

The clock unit 106 is a clock that measures current date and time. For example, the wireless unit 107 is a communication interface communicably connected to the Internet 50 in a wireless manner. For example, the reading unit 108 executes non-contact integrated circuit (IC) communication with the driver's license of the driver, reads out personal information from the driver's license, and based on the personal information being read, identifies the user ID of the driver who is driving the vehicle.

The pulse rate detection unit 109 is a detection unit that detects the pulse rate of the driver. For example, a sensor is installed in a steering wheel of a vehicle that comes into contact with the body of the driver, and the pulse rate of the driver is detected by using such a sensor. The pulse rate detection unit 109 may also detect the pulse rate of the driver, in the same manner as the contact type pulse rate measurement unit such as the ear clip type pulse measurement unit, or the non-contact type pulse rate measurement unit, like the detection unit 11 illustrated in FIG. 2. The pulse rate detection unit 109 may also detect the blood pressure of the driver, in addition to the pulse rate.

For example, the sleepiness sensor 110 is a sensor that detects the sleepiness of the driver of a traveling vehicle. For example, the status switch 111 is a switch that specifies the state of the driver of the vehicle. For example, the status switch 111 is a switch that specifies the state of the driver among the states such as unspecified, loading, unloading, resting, or sleeping. For example, the close call incident reporting switch 112 is a reporting switch to operate when the driver of the traveling vehicle has had a close call. For example, the sleepiness reporting switch 113 is a reporting switch to operate when the driver of the traveling vehicle has felt sleepy. The storage unit 114 is a storage device that stores therein various types of information.

The control unit 120 is a processing unit that controls the entire detection device 100. For example, the control unit 120 associates and collects the detection results detected by the units 101 to 106 and the units 109 to 113, with device identification information that uniquely identifies the units 101 to 106 and the units 109 to 113, as well as the user ID. The control unit 120 then stores the collected information in the storage unit 114. In the following explanation, the information collected by the detection device 100 is referred to as driving information. For example, the control unit 120 corresponds to an acquiring unit.

An example of driving information stored in the storage unit 114 will now be described. FIG. 4 is an exemplary diagram illustrating a data configuration of driving information. As illustrated in FIG. 4, in driving information 114a, a user ID, date and time of measurement, blood pressure, pulse rate, detected sleepiness, and an operation flag are associated with each other. Also, in the driving information 114a, white line deviation, a close call, an offense, tailgating, traveling speed, traveling distance, and engine rotation speed are associated with each other.

The user ID is information to uniquely identify the driver. For example, the date and time of measurement is the date and time measured by the clock unit 106. For example, the blood pressure is blood pressure of the driver collected by the pulse rate detection unit 109. For example, the pulse rate is a pulse rate of the driver collected by the pulse rate detection unit 109. Although not indicated in FIG. 4, the blood pressure and the pulse rate are associated with device identification information that uniquely identifies the pulse rate detection unit 109 having detected the blood pressure and the pulse rate.

The detected sleepiness indicates the operation of the sleepiness reporting switch 113, in other words, whether the driver has felt sleepy. If the driver has felt sleepy, "1" is stored in the driving information 114*a*. Although not indicated in FIG. 4, the detected sleepiness is associated with the device identification information that uniquely identifies the sleepiness reporting switch.

The operation flag corresponds to a flag that indicates whether the driver is in operation. If the operation flag is "1", it indicates that the driver is in operation, when the start of the operation is specified through the status switch 111. If the operation flag is "0", it indicates that the operation is stopped, when the operation is stopped through the status switch 111. Although not indicated in FIG. 4, the operation flag is associated with the device identification information that uniquely identifies the status switch 111.

The white line deviation indicates whether the white line detection unit 104 has detected the white line deviation. For example, if the white line deviation has occurred, "1" is stored in the driving information 114*a*. Although not indicated in FIG. 4, the white line deviation is associated with the device identification information that uniquely identifies the white line detection unit 104.

The close call indicates the operation of the close call incident reporting switch 112, in other words, whether the driver has had a close call. If the driver has had a close call, "1" is stored in the driving information 114*a*. Although not indicated in FIG. 4, the close call is associated with the device identification information that uniquely identifies the close call incident reporting switch 112.

For example, the offense indicates whether an offense such as speeding or sudden acceleration or deceleration is detected and included in the results obtained by the vehicle speed detection unit 101 and the rotation speed detection unit 102. For example, if an offense such as speeding or sudden acceleration or deceleration has occurred, "1" is stored in the driving information 114*a*. The tailgating is a state when the inter-vehicle distance between the preceding vehicle and the own vehicle detected by the inter-vehicle distance detection unit 103 is less than a predetermined distance. If the inter-vehicle distance between the preceding vehicle and the own vehicle becomes less than the predetermined distance, "1" is stored in the driving information 114*a*.

For example, a predetermined event is detected, if the white line deviation is detected, if the offense is detected, or if the inter-vehicle distance becomes less than the predetermined distance.

For example, the traveling speed is a traveling speed of a traveling vehicle in an operating time band, detected by the vehicle speed detection unit 101. For example, the traveling distance is a traveling distance of a traveling vehicle in an operating time band, detected by the vehicle speed detection unit 101. Although not indicated in FIG. 4, the traveling speed and the traveling distance are associated with the device identification information that uniquely identifies the vehicle speed detection unit 101. For example, the engine rotation speed is engine rotation speed of a traveling vehicle in the operating time band, detected by the rotation speed detection unit 102. Although not indicated in FIG. 4, the engine rotation speed is associated with the device identification information that uniquely identifies the rotation speed detection unit 102.

Returning to the explanation of FIG. 3, the determination unit 115 is a processing unit that detects a predetermined event based on the traveling information. When the predetermined event is detected, the determination unit 115 determines the probability of the predetermined event, based on vital sign information of the driver in the proximity of a predetermined time.

The traveling information is information detected by the vehicle speed detection unit 101, the rotation speed detection unit 102, the inter-vehicle distance detection unit 103, the white line detection unit 104, and the like. The vital sign information of the driver is information detected by the pulse rate detection unit 109 and the like.

An example of a process when the determination unit 115 detects a predetermined event will now be described. The determination unit 115 acquires information detected by the vehicle speed detection unit 101 and the rotation speed detection unit 102, and determines whether an offense such as speeding or sudden acceleration or deceleration has occurred. For example, if the speed has exceeded a predetermined speed, if the acceleration speed has exceeded a predetermined acceleration speed, or if the deceleration speed has exceeded a predetermined deceleration speed, the determination unit 115 determines that an offense has occurred. If it is determined that an offense has occurred, "1" is recorded in an item of the offense corresponding to the date and time of measurement in the driving information 114*a*, by the determination unit 115.

The determination unit 115 acquires information detected by the inter-vehicle distance detection unit 103, and determines whether the inter-vehicle distance between the preceding vehicle and the own vehicle has become less than a predetermined distance. If the inter-vehicle distance between the preceding vehicle and the own vehicle has become less than the predetermined distance, "1" is recorded in an item of the tailgating corresponding to the date and time of measurement in the driving information 114*a*, by the determination unit 115.

The determination unit 115 acquires information detected by the white line detection unit 104, and determines whether the white line deviation is detected. If the white line deviation is detected, "1" is recorded in an item of the white line deviation corresponding to the date and time of measurement in the driving information 114*a*, by the determination unit 115.

Subsequently, an example of a process to determine the probability of detecting a predetermined event by the determination unit 115 will now be described. For example, it is assumed that the predetermined event corresponds to the offense, the tailgating, and the white line deviation described above. The determination unit 115 accesses the driving information 114*a*, acquires the vital sign information in the proximity of the date and time of measurement when the predetermined event has occurred, and determines the probability of the predetermined event.

If a value of the vital sign information is different from a normal value, in either before or after, or both before and after the date and time of measurement when the predetermined event is detected, the determination unit 115 determines that the occurrence of the predetermined event is more probable.

In this example, a process in which the determination unit 115 determines the probability using the pulse rate of the driver will be described. The determination unit 115 classifies the probability of detecting an event into one of A, B, and C. The probability A is most probable, and it is assumed that the magnitude relation of probability is probability A>probability B>probability C. For example, as illustrated below, the determination unit 115 classifies the probability, by comparing between the average value of the pulse rate and a threshold value. The average value of the pulse rate is obtained between predetermined seconds before the date and time of measurement when the event is detected, and the date and time of measurement when the event is detected. For example, the magnitude relation of the thresholds can be expressed by T1>T2>T3, and among the thresholds, T1 is the furthest value from the normal pulse rate of a driver. A manager sets the thresholds in advance.

Probability A: T1<average value of pulse rate
Probability B: T2<average value of pulse rate≤T1
Probability C: T3<average value of pulse rate≤T2

In the above description, the average value of the pulse rate is obtained between predetermined seconds before the date and time of measurement when the predetermined event is detected, and the date and time of measurement when the predetermined event is detected. However, it is not limited thereto. For example, the average value of the pulse rate may be obtained between predetermined seconds after the date and time of measurement when the predetermined event is detected, and the date and time of measurement when the predetermined event is detected. The average value of the pulse rate may also be obtained between predetermined seconds before and predetermined seconds after the date and time of measurement when the predetermined event is detected.

Based on the determination result, the determination unit 115 generates event probability information. The determination unit 115 stores the generated event probability information in the storage unit 114. FIG. 5 is an exemplary diagram illustrating a data configuration of event probability information. As illustrated in FIG. 5, the event probability information 114b associates a user ID, event detected date and time, an event, and probability with one another. The user ID is information that uniquely identifies the driver. The event detected date and time corresponds to the date and time of measurement when the predetermined event is detected. The event corresponds to the content of the event. The content of the event includes the offense, the tailgating, and the white line deviation. The probability corresponds to the probability determined by the determination unit 115 described above.

In the above description, the determination unit 115 determines the probability using the pulse rate of the driver. However, it is not limited thereto. For example, the determination unit 115 may determine the probability, based on the sleepiness of the driver output from the sleepiness sensor 110. If the sleepiness of the driver is detected either before or after, or both before and after the date and time of measurement when the predetermined event is detected, the determination unit 115 determines that the occurrence of the predetermined event is more probable. The determination unit 115 may classify the probability in a plurality of levels, based on the level of sleepiness.

The determination unit 115 may also determine the probability by using both the pulse rate of the driver and the sleepiness of the driver. For example, if the driver's sleepiness is detected either before or after, or both before and after the date and time of measurement when the predetermined event is detected, the determination unit 115 determines the probability as "probability A". If the average value of the driver's pulse rate is equal to or more than the threshold, either before or after, or both before and after the date and time of measurement when the predetermined event is detected, the determination unit 115 determines the probability as "probability B".

Figure 6:
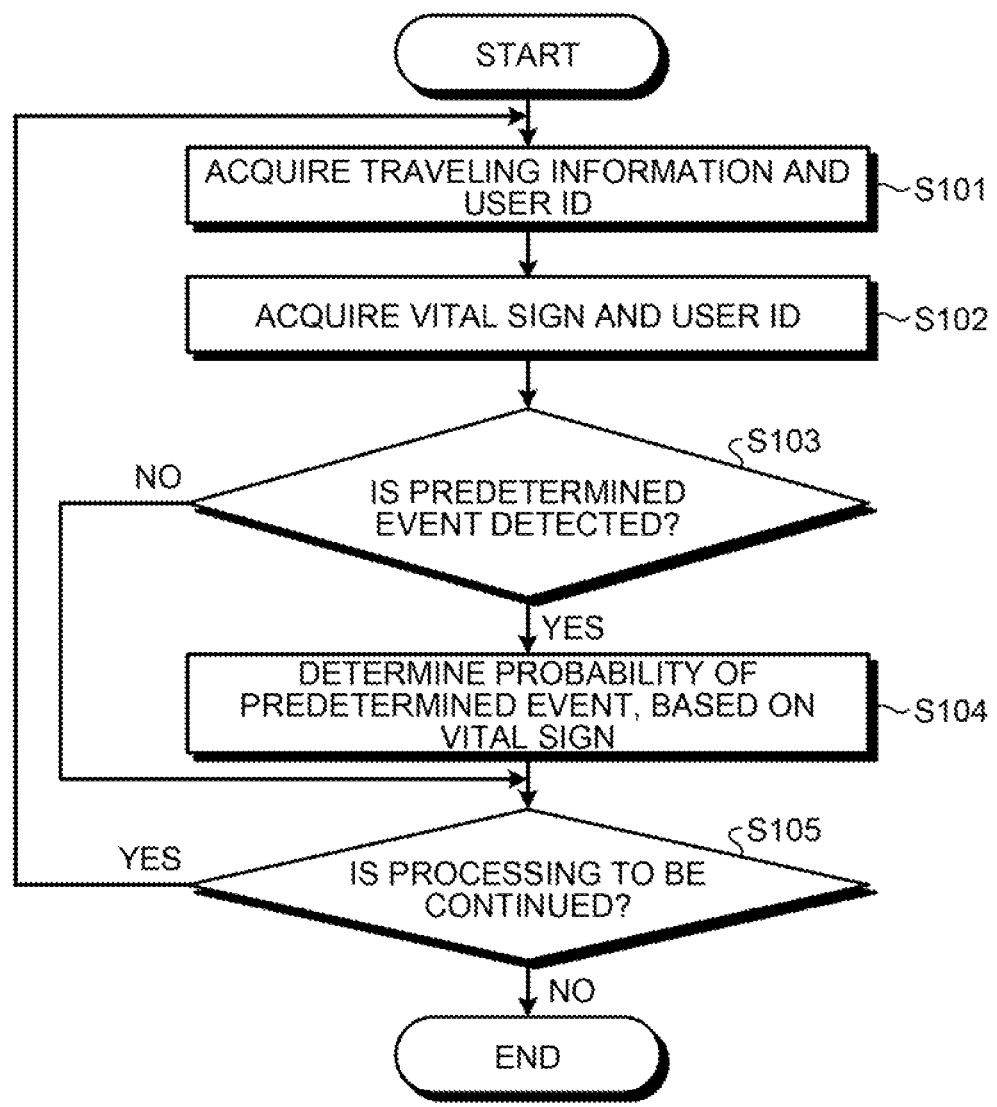
FIG. 6 is an exemplary diagram illustrating a processing procedure of the detection device according to the present embodiment.

Next, an example of a processing procedure of the detection device 100 to the present embodiment will now be described. FIG. 6 is an exemplary diagram illustrating a processing procedure of the detection device according to the present embodiment. As illustrated in FIG. 6, the determination unit 115 or the detection device 100 acquires the traveling information as well as the user ID (step S101). The determination unit 115 acquires the vital sign as well as the user ID (step S102).

The determination unit 115 determines whether a predetermine event is detected (step S103). If the predetermined event is not detected (No at step S103), the determination unit 115 proceeds to step S105.

If the predetermined event is detected (Yes at step S103), the determination unit 115 determines the probability of the predetermined event, based on the vital sign (step S104). The determination unit 115 then determines whether to continue the processing (step S105). If the processing is to be continued (Yes at step S105), the determination unit 115 proceeds to step S101. On the other hand, if the processing is not to be continued (No at step S105), the determination unit 115 finishes the processing.

An effect of the detection device 100 according to the present embodiment will now be described. The detection device 100 acquires the traveling information, the vital sign information, and the user ID of the driver from the vehicle speed detection unit 101, the pulse rate detection unit 109, the storage unit 114, and the like. If a predetermined event is detected at a certain time based on the traveling information, the detection device 100 determines the probability of detecting the predetermined event, based on the vital sign in the proximity of the certain time, and outputs the determination result. For example, if the white line is deviated, if an offence has occurred, or if the inter-vehicle distance becomes less than a predetermined distance, the driver's vital sign becomes different from a normal vital sign. Thus, by using the vital sign, it is possible to determine the probability of the detected predetermined event.

The detection device 100 determines the probability of detecting the predetermined event, based on the vital sign either before or after, or both before and after the certain time. Thus, even if the vital sign fluctuates at the time different from that of the normal time, it is possible to determine the probability of the detected predetermined event.

If the vital sign indicates a value different from the normal value, when the predetermined event is detected in the traveling information, the detection device 100 determines that the occurrence of the event is more probable. Thus, it is possible to improve the determination accuracy of the probability, when the event has occurred.

Figure 7:
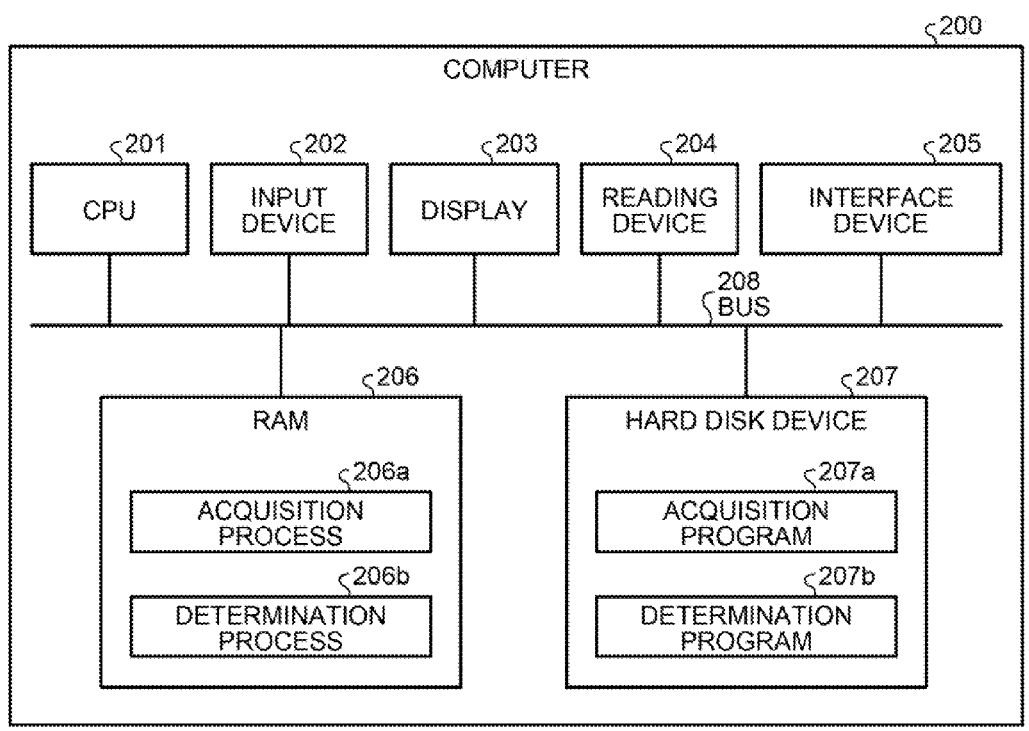
FIG. 7 is an exemplary diagram illustrating a computer that executes a computer program stored in a computer-readable recording medium.

Next, an example of a computer that executes a computer program stored in a computer-readable recording medium that implements the similar functions as those of the detection device 100 illustrated in the embodiment described above will now be explained. FIG. 7 is an exemplary diagram illustrating a computer that executes a computer program stored in a computer-readable recording medium.

As illustrated in FIG. 7, a computer 200 includes a central processing unit (CPU) 201 that executes various computation processes, an input device 202 that receives an input of data from a user, and a display 203. The computer 200 includes a reading device 204 that reads out a computer program and the like from the storage medium, and an interface device 205 that transmits and receives data to and from another computer via a network. The computer 200 also includes a random-access memory (RAM) 206 that temporarily stores therein various types of information, and a hard disk device 207. The devices 201 to 207 are connected to a bus 208.

The hard disk device 207 reads an acquisition program 207a and a determination program 207b into the RAM 206. The acquisition program 207a functions as an acquisition process 206a. The determination program 207b functions as a determination process 206b. For example, the acquisition process 206a corresponds to the control unit 120. The determination process 206b corresponds to the determination unit 115.

The acquisition program 207a and the determination program 207b need not be stored in the hard disk device 207 from the beginning. For example, the acquisition program 207a and the determination program 207b may be stored in a "portable physical medium" such as a flexible disk (FD), a compact disc-read only memory (CD-ROM), a digital versatile disc (DVD), a magneto optical disk, and an integrated circuit (IC) card that can be inserted into the computer 200. The computer 200 can then read out the acquisition program 207a and the determination program 207b and execute them.

It is possible to determine the probability of the detected predetermined event.

All examples and conditional language recited herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although the embodiment of the present invention has been described in detail, it should be understood that the various changes, substitutions, and alterations could be made hereto without departing from the spirit and scope of the invention.

What is claimed is:

1. A non-transitory computer-readable recording medium having stored therein a program that causes a computer to execute a process, comprising:
   acquiring traveling information and identification information of a driver from a first device installed in a vehicle;
   acquiring a vital sign and the identification information of the driver from a second device that monitors the vital sign;
   determining probability of detecting a predetermined event as being more probable, based on the vital sign in proximity of a certain time indicating a value different from a normal value, when the predetermined event is detected at the certain time based on the traveling information; and
   outputting a determination result.

2. The non-transitory computer-readable recording medium according to claim 1, wherein the proximity is either before or after, or both before and after the certain time.

3. A detection method comprising:
   acquiring traveling information and identification information of a driver from a first device installed in a vehicle, using a processor;
   acquiring a vital sign and the identification information of the driver from a second device that monitors the vital sign, using the processor;
   determining probability of detecting a predetermined event as being more probable, based on the vital sign in proximity of a certain time indicating a value different from a normal value, when the predetermined event at the certain time is detected based on the traveling information being acquired, using the processor; and
   outputting a determination result, using the processor.

4. The detection method according to claim 3, wherein the proximity is either before or after, or both before and after the certain time.

5. A detection device, comprising:
   a processor that executes a process comprising:
   acquiring traveling information and identification information of a driver from a first device installed in a vehicle;
   acquiring a vital sign and the identification information of the driver from a second device that monitors the vital sign;
   determining probability of detecting a predetermined event as being more probable, based on the vital sign in proximity of a certain time indicating a value different from a normal value, when the predetermined event is detected at the certain time based on the traveling information;
   outputting a determination result.

6. The detection device according to claim 5, wherein the proximity is either before or after, or both before and after the certain time.

* * * * *